United States Patent [19]

Samsel

[11] Patent Number: 5,597,937
[45] Date of Patent: Jan. 28, 1997

[54] CONVERSION OF DEEP INTERNAL OLEFINS INTO PRIMARY ALKYLALUMINUM COMPOUNDS BY ISOMERIZATION-DISPLACEMENT

[75] Inventor: Edward G. Samsel, Baton Rouge, La.

[73] Assignee: Albemarle Corporation, Richmond, Va.

[21] Appl. No.: 438,686

[22] Filed: May 11, 1995

[51] Int. Cl.$^6$ .................................................. C07F 5/06
[52] U.S. Cl. ............................................................ 556/190
[58] Field of Search ............................................. 556/190

[56] References Cited

U.S. PATENT DOCUMENTS

| | | | |
|---|---|---|---|
| 3,322,806 | 5/1967 | Asinger et al. | 260/448 |
| 3,445,494 | 5/1969 | Acciarri | 260/448 |
| 3,474,122 | 10/1969 | Ichiki et al. | 260/448 |
| 3,475,477 | 10/1969 | Muller et al. | 260/448 |
| 4,111,662 | 9/1978 | Masotti et al. | 422/231 |
| 4,251,453 | 2/1981 | Garrison | 260/448 A |

FOREIGN PATENT DOCUMENTS

| | | |
|---|---|---|
| 0751921 | 1/1967 | Canada . |
| 0844590 | 8/1960 | United Kingdom . |

OTHER PUBLICATIONS

Asinger, F.; Fell, B.; Janssen, R. *Chem. Ber.* 1964, 97 2515–20.

Asinger, F.; Fell, B.; Osberghaus, R. Ibid. 1971, 104, 1332–4.

*Primary Examiner*—Porfirio Nazario-Gonzalez
*Attorney, Agent, or Firm*—Philip M. Pippenger

[57] ABSTRACT

A deep olefin internal olefin is reacted with a $C_{3-4}$ primary alkyl aluminum chloride in the liquid phase in the presence of a catalyst system formed from (i) a dicyclopentadienyl dihalide or halohydride of zirconium or hafnium and (ii) a hydridic co-catalyst component. Unlike prior art procedures, negligible quantities of by-product paraffins are formed in the process.

24 Claims, No Drawings

5,597,937

CONVERSION OF DEEP INTERNAL OLEFINS INTO PRIMARY ALKYLALUMINUM COMPOUNDS BY ISOMERIZATION-DISPLACEMENT

TECHNICAL FIELD

This invention relates to novel process technology enabling the transformation of deep internal olefins into alkyl aluminum compounds having at least one primary linear alkyl group derived from the internal olefin. As used herein, the term "olefin" refers to monoolefins, and the term "deep internal" with respect to olefins means that the olefin has its double bond no closer to any terminal position than the 3-position.

BACKGROUND

Studies on the catalyzed hydroalumination of deep internal olefins to produce terminally bonded aluminum alkyls were conducted by Asinger et al. in the 1960's. See, Asinger, F.; Fell, B.; Janssen, R. *Chem. Ber.* 1964, 97, 2515–20; Asinger, F.; Fell, B.; Osberghaus, R. Ibid. 1971, 104, 1332–4; Asinger et al. U.S. Pat. No. 3,322,806 (1967); and Muller, et al. U.S. Pat. No. 3,475,477 (1969). Those studies used as catalysts salts and alkoxides of transition metals, especially titanium and zirconium acting on triisobutyl aluminum. Unfortunately, and although unrecognized at the time, those reactions gave substantial amounts ($\geq 10\%$ yield) of paraffin side products, as shown by subsequent studies at these laboratories.

Relatively economical processes for producing deep internal olefins are well known in the art. Thus, process technology enabling the conversion of deep internal olefins into terminally bonded aluminum alkyls with minimal paraffin by-product formation would be a most welcome contribution to the art, especially if the process results in high yields of the desired products.

THE INVENTION

Novel process technology has now been discovered which enables the production of terminally bonded aluminum alkyls while avoiding the formation of excessive amounts of paraffinic by-products. Experimental work on the process of this invention has shown that only minimal amounts ($\leq 1\%$) of paraffin were formed. In addition experiments have been carried out wherein portions of the alkyl aluminum product were isolated and hydrolyzed with $DCl/D_2O$. The recovered alkane was shown by $^{13}CNMR$ to be deuterated exclusively on the primary carbon atom, within the limits of detection. The invention thus makes possible the highly selective conversion of deep internal olefins into terminal aluminum alkyls which can be used either as catalyst components or as intermediates for the production of 1-olefins, primary alcohols, and other useful end products. Moreover, yields as high as 87% (based on available aluminum sites) have been achieved.

In accordance with one of its embodiments this invention provides a process of converting at least one deep internal linear olefin having at least 6 carbon atoms in the molecule into at least one alkyl aluminum compound having at least one primary linear alkyl group derived from the olefin by reacting the deep internal olefin with a $C_{3-4}$ primary alkyl aluminum chloride in the liquid phase in the presence of a catalyst system formed from (i) a dicyclopentadienyl metal dihalide (preferably a dicyclopentadienyl metal dichloride) and/or a dicyclopentadienyl metal halohydride (preferably a dicyclopentadienyl metal chlorohydride), wherein the metallic constituent thereof is zirconium or hafnium and (ii) a hydridic co-catalyst component.

Another embodiment of this invention is a two stage process in which the first stage is conducted as described above, and in which the second stage involves reacting the resultant alkyl aluminum compound having at least one primary linear alkyl group derived from the original deep internal olefin with ethylene or propylene under thermal or catalytic displacement conditions to form an olefin product enriched in linear 1-olefin having at least 6 carbon atoms.

A preferred embodiment of this invention is a process which comprises:

(a) heating at least one deep internal linear olefin having at least 6 carbon atoms in the molecule with a mixture of di(n-propyl) aluminum chloride and tri-n-propyl aluminum in the liquid phase in the presence of a catalyst system formed from (i) a dicyclopentadienyl metal dihalide (preferably a dicyclopentadienyl metal dichloride) and/or a dicyclopentadienyl metal halohydride (preferably a dicyclopentadienyl metal chlorohydride), wherein the metallic constituent thereof is zirconiumor hafniumand (ii) a hydridic co-catalyst component to form at least one alkyl aluminum compound having at least one primary linear alkyl group derived from the deep internal olefin;

(b) reacting the resultant alkyl aluminum compound with propylene under thermal or catalytic displacement conditions to form a reaction product comprising linear 1-olefin having at least 6 carbon atoms, di(n-propyl) aluminum chloride and tri(n-propyl) aluminum; and (c) recycling di(n-propyl) aluminum chloride and tri(n-propyl) aluminum to (a).

These and other embodiments and features of this invention will become still further apparent from the ensuing description and appended claims.

Deep Internal Olefin

The deep internal olefins which undergo the isomerization in the hydroalumination reaction of this invention have at least six carbon atoms per molecule and can be individual olefins or mixtures of two or more such olefins. The process is preferably applied to linear olefinic hydrocarbons wherein the double bond is no closer to any terminal position than the 3-position. The most preferred olefins which are isomerized pursuant to this invention are straight chain olefins typified by such compounds as 3-hexene, 3-heptene, 3-octene, 4-octene, 3-nonene, 4-nonene, 3-decene, 4-decene, 5-decene and analogous higher homologs which may contain up to about 36 carbon atoms, but more preferably no more than about 24 carbons atoms, and still more preferably no more than about 12 carbons atoms. Less preferred are suitably branched olefins such as 2-methyl-3-heptene, 3-methyl-3-heptene, 4-methyl-3-heptene, 5-methyl-3-heptene, 6-methyl-3-heptene, 2,5-dimethyl-3-hexene, and similar branched higher homologs which likewise may contain up to about 36 carbon atoms, but more preferably no more than about 24 carbons atoms, and still more preferably no more than about 12 carbons atoms. It will be understood and appreciated that the deep internal olefins which are isomerized into terminal aluminum alkyls pursuant to this invention can be in admixture with other olefins such as 1-olefins and 2-olefins. The 2-olefins will be also be isomerized into terminal aluminum alkyls in the process and the 1-olefins tend to form terminal aluminum alkyls at the outset. Thus in all cases wherein a linear olefin mixture containing both deep olefins and 1- and 2-olefins is used as the initial feed in the process of this invention, the aluminum alkyl product formed therefrom will contain a larger mol percentage of terminal alkyl groups than the mol percentage of 1- and 2-olefins in the initial olefin mixture. Most preferably, the olefins used in the process are (a) 3-hexene, (b) a mixture of hexenes containing at least 10 mol % of 3-hexene, (c) 3-decene, (d) 4-decene, (e) 5-decene, (f) a mixture of at least two of (c), (d) and (e); and (g) a mixture of hexenes containing at least 10 mol % of any of (c), (d), (e) or (f).

Primary Alkyl Aluminum Chloride

The $C_{3-4}$ primary alkyl aluminum chloride used in the process is exemplified by di(n-propyl) aluminum chloride, di(n-butyl) aluminum chloride, diisobutyl aluminum chloride, and mixtures thereof such as a mixture of di(n-propyl) aluminum chloride and diisobutyl aluminum chloride, or a mixed product such as isobutyl aluminum sesquichloride, as well as similar mixed compounds. Higher homologs such as di(pentyl) aluminum chloride can be used either alone or in admixture with one or more $C_{3-4}$ primary alkyl aluminum chlorides, if desired. While the chlorides are distinctly preferred, other $C_{3-4}$ primary alkyl aluminum halides—i.e., the fluorides, bromides and iodides—may be used. Of the alkyl aluminum halides the most preferred are di(n-propyl) aluminum chloride and diisobutyl aluminum chloride.

The alkyl aluminum halide may be used in combination with one or more primary trialkyl aluminum compounds, which preferably contain 3 or 4 carbon atoms in each alkyl group. Examples of such compounds include tripropyl aluminum, tributyl aluminum, triisobutyl aluminum, tripentyl aluminum, tri(2-methylbutyl) aluminum, tri(3-methylbutyl) aluminum, and the like. The use of a combination of primary alkyl aluminum chloride and primary trialkyl aluminum offers the advantage of greater equipment productivity as compared to an equimolar quantity of the primary alkyl aluminum chloride.

Dicyclopentadienyl Metal Compound

These components of the catalyst systems used in the practice of this invention are compounds of the formula $R_2MXY$ wherein R is a cyclopentadienyl or indenyl group which may be ring-substituted, M is zirconium or hafnium, most preferably zirconium, X is a halogen atom—i.e., a fluorine, chlorine, bromine or iodine atom, preferably a chlorine atom—and Y is a halogen atom or a hydrogen atom, preferably a chlorine atom or a hydrogen atom, and most preferably a chlorine atom. The cyclopentadienyl-moiety containing group (which also has been referred to as a cyclomatic group) typically contains from 5 to about 18 carbon atoms, and preferably from 5 to about 12 carbon atoms. The two cyclopentadienyl groups may be bonded together by a bridge as in the case of a racemic mixture of two indenyl groups bonded together by a dimethylene bridge (i.e., a compound which can be represented as rac-$(CH_2)_2Ind_2ZrCl_2$). Examples of suitable compounds include dicyclopentadienyl zirconium dichloride; ring alkyl-substituted dicyclopentadienyl zirconium dichlorides which may be symmetrical or asymmetrical such as the symmetrical compounds bis(methylcyclopentadienyl) zirconium dichloride, bis(dimethylcyclopentadienyl) zirconium dichloride, bis(trimethylcyclopentadienyl) zirconium dichloride, bis(tetramethylcyclopentadienyl) zirconium dichloride, bis(pentamethylcyclopentadienyl) zirconium dichloride, and corresponding ethyl, propyl, butyl, pentyl, hexyl, etc., ring-substituted biscyclopentadienyl zirconium dichlorides, bisindenyl zirconium dichloride, bis(methylindenyl) zirconium dichloride, and the asymmetrical compounds such as (cyclopentadienyl)(methylcyclopentadienyl) zirconium dichloride, (cyclopentadienyl) (ethylcyclopentadienyl) zirconiumdichloride, (ethylcyclopentadienyl) (methylcyclopentadienyl) zirconium dichloride, and like compounds. Another subgroup is made up of ring alkylsilyl-substituted dicyclopentadienyl zirconium dichlorides, which also can be symmetrically or unsymmetrically substituted such as bis-(dimethylsilylcyclopentadienyl) zirconium dichloride, bis(t-rimethylsilylcyclopentadienyl) zirconium dichloride, bis-(butylsilylcyclopentadienyl) zirconium dichloride, (cyclopentadienyl) (dimethylsilylcyclopentadienyl) zirconium dichloride, and analogous compounds. Compounds corresponding to any of the foregoing wherein one or both of the chlorine atoms are replaced by other halogen atoms are suitable. A few such compounds include dicyclopentadienyl zirconium difluoride, dicyclopentadienyl zirconium dibromide, dicyclopentadienyl zirconium diiodide, and dicyclopentadienyl zirconium chlorobromide. Also suitable are related monochloride derivatives such as dicyclopentadienyl zirconium chlorohydride. Compounds corresponding to any of the foregoing in which the metal constituent is hafnium are also suitable. Of the ring-alkyl substituted compounds, those having less than 5 ring substituents are preferred. The bis(monoalkyl) substituted compounds are the most preferred of the ring substituted compounds.

Hydridic Co-catalyst Component

This component used in forming the catalyst system can be an alkyl aluminum hydride such as a dialkyl aluminum hydride or an alkyl aluminum sesquihydride; or an alkali or alkaline earth metal aluminum hydride such as lithium aluminum hydride, sodium aluminum hydride, potassium aluminum hydride, magnesium aluminum hydride, calcium aluminum hydride, a lithium dialkoxide dihydride, a sodium dialkoxide dihydride, or the like. The alkyl aluminum hydrides are preferred, and these can be added to the initial reaction mixture as preformed components or they can be formed in situ by addition to the initial reaction mixture of a trialkyl aluminum compound that tends to readily undergo thermal displacement of an alkyl group, such as triisobutyl aluminum. Most preferred as the hydridic component is diisobutyl aluminum hydride.

Active Catalytic Species

The composition of the one or more actual active catalyst species in the process has not been identified. It has been observed, however, that the reaction mixtures tend to become highly colored during the course of the reaction. For example, the reaction mixture becomes deep red when diisobutyl aluminum chloride is used as an initial component, and purple when dipropyl aluminum chloride is used as an initial component in forming the catalyst. The color starts to develop a few minutes after applying heat to the initial reaction mixture.

Reaction Diluent

As noted above, the reaction is conducted in the liquid phase. Thus unless the feed olefin is in the liquid state at the reaction temperatures employed, it is preferred to conduct the reaction using an inert diluent, most preferably an inert hydrocarbon diluent such as a paraffinic, cycloparaffinic or aromatic hydrocarbon or mixture of two or more of such hydrocarbons. A few illustrative examples include one or more isomeric forms of heptane, octane, nonane or decane; cycloparaffins such as cyclopentane, methylcyclopentane, cyclohexane, or cycloheptane; and aromatics such as toluene, one or more xylene isomers, tetrahydronaphthalene, and commercially available mixtures of suitable boiling points such as gasoline fractions, petroleum ethers, mixed alkanes, mixed cycloalkanes and mixed mononuclear aromatic hydrocarbons. It is preferred to use as the reaction diluent, or at least to include in the reaction diluent, one or more hydrocarbons that boil at the reaction temperature(s) selected and thus can serve as a chaser to assist in the removal from the reaction zone of by-product olefin liberated from the initial alkyl aluminum component(s) as the reaction proceeds. Toluene and heptane have been successfully used for this purpose.

Reaction Conditions

The reaction tends to initiate rapidly and slow down as the reaction proceeds. Thus the reaction is preferably conducted for a time sufficient to achieve a suitable yield of the desired product at the particular reaction temperature(s) selected for use. Generally speaking, preferred conditions include use of temperatures in the range of about 120° to about 150° C. for about 6 to about 20 hours. However, times and/or temperatures outside of these ranges can be used whenever deemed necessary or desirable under the given set of circumstances under consideration.

Often the olefin fed to the process is used in a substantial excess relative to the amount of alkyl aluminum chloride used. Thus these materials may be employed in molar ratios of olefin feed to alkyl aluminum chloride ranging from about 1:1 to about 10:1, and preferably from about 2.5:1 to about 5:1. The reactants may be fully charged at the outset of the reaction or one or both may be added portionwise as the reaction proceeds. The excess olefin can be recovered for recycle at the end of the reaction by distillation or other means. It is essentially free of paraffin by-products.

The amount of the catalyst components charged to the reaction mixture can likewise be varied in order to give optimal results with the materials and under the operating conditions selected for use. Typically from about 0.001 to about 0.1 mol of the dicyclopentadienyl metal dihalide or halohydride and up to about 1 mol of the hydridic reagent are charged per mol of alkyl aluminum chloride. Preferably, from about 0.01 to about 0.03 mol of the dicyclopentadienyl metal dihalide or halohydride and from about 0.05 to about 0.4 mol of the hydridic reagent are used per mol of alkyl aluminum chloride. When also including a trialkyl aluminum component in the reaction mixture, the amount thereof typically ranges up to about 2 mols thereof, and preferably up to about 1 mol thereof per mol of the alkyl aluminum chloride reactant. When triisobutyl aluminum is used it may be possible to eliminate the alkyl aluminum chloride, although such a procedure is not preferred.

These catalyst components may be charged in toto at the outset or they may be added portionwise during the course of the reaction.

Second Stage Reactions

In the embodiments of the invention wherein the alkyl aluminum product is reacted with ethylene or propylene in order to displace the alkyl groups as 1-olefin and form ethyl aluminum or propyl aluminum co-product(s), thermal or catalytic displacement conditions are used. In either case an excess of the ethylene or propylene is used. Thermal displacement is generally conducted at temperatures in the range of about 280° to about 320° C. and preferably at temperatures in the range of about 280° to about 300° C., followed by rapid cooling to about 120° C. to prevent excessive isomerization and other undesired side reactions. For further details concerning thermal displacements reference may be had for example to U.S. Pat. No. 3,391,219, the entire disclosure of which is incorporated herein by reference. The catalytic displacements are typically performed at temperatures in the range of about −10° to about 150° C. and preferably in the range of about 20° to about 90° C. Preferred catalysts include nickel and nickel compounds such as nickel naphthenate, nickel bis(acetylacetonate), nickelocene, bis(1,5-cyclo-octadiene)nickel, nickel octylacetoacetate complex, and similar nickel compounds or complexes which are soluble in organic media. Amounts of the displacement catalyst typically fall in the range equivalent to about 1 to about 100 parts by weight of nickel per million parts of reaction mixture. For further details concerning nickel catalyzed displacements see U.S. Pat. No. 4,918,254, the entire disclosure of which is incorporated herein by reference. Other suitable displacement catalysts have been reported in the literature.

To further illustrate the practice and advantages of this invention, the following non-limiting examples are set forth. In these examples, several different reaction procedures were used to facilitate separation of the product gases from the reaction mixtures.

Methods 1 and 2 utilize a Schlenk test-tube (~18 mm OD×90 mm) fitted with teflon valve side arm through which aliquots can be withdrawn by syringe under inert gas purge. A nitrogen adapter is fitted to the top by a ST 14/20 joint. The side arm is connected to a manifold containing $N_2$ or Ar and is closed during the reaction. In Method 1, the adapter is connected by a short hose to a silicone oil bubbler and the reaction is conducted at 1 atm of $N_2$ or Ar. In Method 2, the hose is connected to a liq. $N_2$ trap and by a Tee connector to a vacuum control valve (Matheson 3491), which is connected to a vacuum/nitrogen dual manifold. Reactions are conducted under a static vacuum of 200–250 mmHg of nitrogen. In these reactions, gaseous olefins are evolved from a mixture in which the olefin reactant is the most volatile additive.

In Method 3, a 50 or 100 mL round bottom Schlenk flask is connected by a ST 24/40 joint to a distillation apparatus containing a five glass plate jacketed Oldershaw column. The receiver is connected by a short hose to an oil bubbler, and the reactions are conducted under 1 atm of nitrogen with the side arm of the Schlenk flask sealed. This side arm is a 90° vacuum valve where the valve plug can be removed to withdraw aliquots under $N_2$ purge. In this method a volatile chaser, toluene or heptane, is added to the reaction so that reflux occurs in the column. Example i below involves use of Method 3.

EXAMPLE 1

A 100 mL Schlenk flask is loaded with tri-n-propyl aluminum (3.27 g), toluene (10 mL) and $AlCl_3$ (1.15 g). After slow dissolution with chilling, a solution of di (n-propyl) aluminum chloride (25.8 mmol of Al) is formed. To this is added diisobutyl aluminum hydride (0.500 mL, 2.81 mmol of Al, totaling 59.9 mmol of al-C sites) , 5-decene (22.4 mL, 118 mmol) , undecane (10.0 mL) and di(cyclopentadienyl) zirconium dichloride (173 mg, 0.592 mmol). The flask is attached to the distillation apparatus in a glove box, then attached to a Schlenk dual manifold in a hood, and to an oil bubbler. The colorless solution is heated in a 165° C. oil bath to reflux toluene into the column. After a few minutes, purple color forms and gas evolution is noted. The flask is cooled and aliquots are taken at 3, 6 and 22 hours. The aliquots, diluted in toluene, are hydrolyzed under $N_2$ with degassed 10% aqueous HCl. In a run carried out in this manner, GC analysis showed n-decane: 30.0, 35.0 and 47.0 mmol, respectively.

EXAMPLES 2–14

The general synthesis procedure of Example 1 is repeated using the materials and quantities set forth in the following table. The respective products are formed using whichever of Methods 1–3 is specified in the table. In Example 4, a second charge of the catalyst components is made after 3 hours of reaction, and no chaser is employed. The chaser in Examples 7 and 9 is 10 mL of toluene. In Examples 12 and 13 the chaser is 5 mL of toluene whereas 5 mL of heptane is the chaser in Example 14. In each case except Example 8, the deep internal linear olefin reactant used is 5-decene. In Example 8, the olefin reactant is mixed decene isomers formed by isomerization of 5-decene. A second addition of the hydridic co-catalyst component is made after 3 hours of reaction in Example 11.

For convenience, the following abbreviations are used in the table:

DNPAC=di-n-propyl aluminum chloride
DIBAC=diisobutyl aluminum chloride
DIBAH=diisobutyl aluminum hydride
LAH=lithium aluminum hydride
TNPA=tri-n-propyl aluminum
10-Zr=di(cyclopentadienyl) zirconium dichloride
18-Zr=di(n-butylcyclopentadienyl) zirconium dichloride
20-Zr=rac-$(CH_2)_2Ind_2ZrCl_2$

| Example No. | Catalyst, mmol | Co-catalyst, mmol Al | 5-Decene, mmol | Alkyl Al Chloride, mmol Al | Temp., °C. | Reaction Method | Time, hrs. | n-Decyl Al, mmol | Yield, % |
|---|---|---|---|---|---|---|---|---|---|
| 2 | 10-Zr, 0.051 | DIBAH, 1.24 | 10.6 | DNPAC, 3.00 | 120 | 2 | 1.5 | 1.79 | 19 |
|   |   |   |   |   |   |   | 3 | 2.47 | 26 |
|   |   |   |   |   |   |   | 6 | 3.34 | 36 |
| 3 | 10-Zr, 0.034 | DIBAH, 0.56 | 10.6 | DNPAC, 3.013 | 150 | 1 | 3 | 1.89 | 24 |
|   |   |   |   |   |   |   | 6 | 2.34 | 30 |
| 4 | 10-Zr, 0.68, 0.50 | DIBAH, 2.81, 2.81 | 184.6 | DIBAC, 51.6 | 120 | 3 | 3 | 39.3 | 35 |
|   |   |   |   |   |   |   | 10 | 74.9 | 67 |
| 5 | 10-Zr, 0.038 | LAH, 0.50 | 7.91 | DIBAC, 1.44 | 120 | 1 | 3 | 2.18 | 50 |
|   |   |   |   |   |   |   | 6 | 2.61 | 60 |
| 6 | 10-Zr, 0.038 | DIBAH, 0.28 | 7.91 | DIBAC, 1.44 | 120 | 1 | 3 | 2.02 | 54 |
|   |   |   |   |   |   |   | 6 | 2.65 | 61 |
| 7 | 10-Zr, 0.523 | DIBAH, 2.81 | 118 | DIBAC, 25.8 | ca. 150 | 3 | 6 | 52.15 | 87 |
| 8 | 10-Zr, 0.038 | DIBAH, 0.28 | 7.91, mixed isomers | DIBAC, 1.44 | 120 | 1 | 0 | 0.14 | 0 |
|   |   |   |   |   |   |   | 3 | 2.62 | 67 |
|   |   |   |   |   |   |   | 6 | 3.10 | 79 |
| 9 | 10-Zr, 0.592 | DIBAH, 2.81 | 118 | DNPAC, 51.5 | ca. 150 | 3 | 3 | 30.0 | 50 |
|   |   |   |   |   |   |   | 6 | 35.0 | 58 |
|   |   |   |   |   |   |   | 22 | 47.0 | 78 |
| 10 | 10-Zr, 0.592 | LAH, 2.8 | 118 | DNPAC, 51.5 | ca. 150 | 3 | 3 | 29.6 | 57 |
|   |   |   |   |   |   |   | 6 | 35.1 | 68 |
| 11 | 10-Zr, 0.592 | DIBAH, 2.81, 2.81 | 118 | DNPAC, 51.5 | ca. 150 | 3 | 3 | 26.8 | 45 |
|   |   |   |   |   |   |   | 6 | 36.1 | 53 |
|   |   |   |   |   |   |   | 22 | 42.3 | 62 |
| 12 | 20-Zr, 0.257 | DIBAH, 1.40 | 64.4 | DNPAC, 12.9 | ca. 150 | 3 | 3 | 17.7 | 59 |
|   |   |   |   |   |   |   | 6 | 20.6 | 69 |
| 13 | 18-Zr, 0.337 | DIBAH, 1.40 | 64.4 | DNPAC, 12.9 + TNPA, 1.31 | ca. 150 | 3 | 3 | 17.1 | 51 |
|   |   |   |   |   |   |   | 6 | 20.4 | 61 |
| 14 | 18-Zr, 0.325 | DIBAH, 1.40 | 65.9 | DNPAC, 12.9 + TNPA, 1.31 | ca. 130 | 3 | 3 | 16.1 | 48 |
|   |   |   |   |   |   |   | 6 | 17.9 | 53 |
|   |   |   |   |   |   |   | 22 | 22.4 | 67 |

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

I claim:

1. A process of converting at least one deep internal linear olefin having at least 6 carbon atoms in the molecule into at least one alkyl aluminum compound having at least one primary linear alkyl group derived from said olefin, said process comprising reacting said olefin with a $C_{3-4}$ primary alkyl aluminum chloride in the liquid phase in the presence of a catalyst system formed from (i) a dicyclopentadienyl metal dihalide and/or a dicyclopentadienyl metal halohydride wherein the metallic constituent thereof is zirconium or hafnium and (ii) a hydridic co-catalyst component.

2. A process according to claim 1 wherein said olefin consists essentially of 3-hexene.

3. A process according to claim 1 wherein said olefin consists essentially of 3-octene, 4-octene or a mixture thereof.

4. A process according to claim 1 wherein said olefin consists essentially of 3-decene, 4-decene, 5-decene or a mixture of at least two of the foregoing.

5. A process according to claim 1 wherein said olefin consists essentially of (a) 3-hexene in a mixture of hexenes, (b) 3-octene, 4-octene or both in a mixture of octenes, or (c) 3-decene, 4-decene, 5-decene or a combination of at least two of these in a mixture of decenes.

6. A process according to claim 1 wherein said $C_{3-4}$ primary alkyl aluminum chloride is diisobutyl aluminum chloride.

7. A process according to claim 1 wherein said $C_{3-4}$ primary alkyl aluminum chloride is dipropyl aluminum chloride.

8. A process according to claim 1 wherein the metal constituent of (i) thereof is zirconium.

9. A process according to claim 1 wherein (i) thereof is a dicyclopentadienyl metal dichloride and/or a dicyclopentadienyl metal chlorohydride wherein the metallic constituent thereof is zirconium or hafnium.

10. A process according to claim 1 wherein (i) thereof is dicyclopentadienyl zirconium dichloride.

11. A process according to claim 1 wherein (i) thereof is a ring alkyl-substituted dicyclopentadienyl zirconium dichloride.

12. A process according to claim 1 wherein (i) thereof is a ring alkylsilyl-substituted dicyclopentadienyl zirconium dichloride.

13. A process according to claim 1 wherein (i) thereof is a diindenyl dicyclopentadienyl zirconium dichloride.

14. A process according to claim 1 wherein (i) thereof is rac-$(CH_2)_2Ind_2ZrCl_2$.

15. A process according to claim 1 wherein said hydridic cocatalyst component is formed in situ from triisobutyl aluminum.

16. A process according to claim 1 wherein said hydridic cocatalyst component is an alkyl aluminum hydride.

17. A process according to claim 1 wherein said hydridic cocatalyst component is an alkali metal aluminum hydride.

18. A process according to claim 1 wherein the reaction is conducted in an inert liquid reaction diluent.

19. A process according to claim 18 wherein the inert liquid reaction diluent is an aromatic hydrocarbon diluent.

20. A process according to claim 18 wherein the reaction is conducted in a refluxing reaction mixture.

21. A process according to claim 1 wherein said olefin consists essentially of (a) 3-hexene in a mixture of hexenes, (b) 3-octene, 4-octene or both in a mixture of octenes, or (c) 3-decene, 4-decene, 5-decene or a combination of at least two of these in a mixture of decenes; wherein said $C_{3-4}$ primary alkyl aluminum chloride is diisobutyl aluminum chloride or dipropyl aluminum chloride; wherein the metal constituent of (i) is zirconium; and wherein the reaction is conducted in a refluxing inert liquid reaction diluent.

22. A process according to claim 21 wherein said hydridic cocatalyst component is an alkyl aluminum hydride.

23. A process according to claim 21 wherein said hydridic cocatalyst component is a lithium aluminum hydride.

24. A process according to claim 21 wherein a trialkyl aluminum compound is included in the reaction mixture.

* * * * *